United States Patent
Keaffaber et al.

(10) Patent No.: US 9,763,895 B2
(45) Date of Patent: *Sep. 19, 2017

(54) TINCTURE FOR INFUSING FLAVONOIDS AND METHODS OF USE

(71) Applicant: Heart Healthy Spirits, LLC, Gainesville, FL (US)

(72) Inventors: Jeffrey J. Keaffaber, Gainesville, FL (US); Kim A. Popejoy, Gainesville, FL (US)

(73) Assignee: Heart Healthy Spirits, LLC, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/148,825

(22) Filed: May 6, 2016

(65) Prior Publication Data

US 2016/0250157 A1    Sep. 1, 2016

Related U.S. Application Data

(63) Continuation-in-part of application No. 14/815,085, filed on Jul. 31, 2015, now Pat. No. 9,358,216.

(60) Provisional application No. 62/032,536, filed on Aug. 2, 2014.

(51) Int. Cl.
| | | |
|---|---|---|
| A61K 31/05 | (2006.01) |
| A61K 47/10 | (2017.01) |
| A61K 8/34 | (2006.01) |
| A61K 9/48 | (2006.01) |
| A23L 2/52 | (2006.01) |
| A61K 8/49 | (2006.01) |
| A61K 8/11 | (2006.01) |
| A61K 47/22 | (2006.01) |
| A61K 9/00 | (2006.01) |
| A61K 31/00 | (2006.01) |
| A23L 33/105 | (2016.01) |
| A61K 8/46 | (2006.01) |
| A61Q 19/00 | (2006.01) |
| A23L 33/10 | (2016.01) |

(52) U.S. Cl.
CPC ................ *A61K 31/05* (2013.01); *A23L 2/52* (2013.01); *A23L 33/10* (2016.08); *A23L 33/105* (2016.08); *A61K 8/11* (2013.01); *A61K 8/34* (2013.01); *A61K 8/347* (2013.01); *A61K 8/46* (2013.01); *A61K 8/498* (2013.01); *A61K 9/0095* (2013.01); *A61K 31/00* (2013.01); *A61K 47/10* (2013.01); *A61Q 19/00* (2013.01); *A23V 2002/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 9,358,216 B2 * | 6/2016 | Keaffaber | A61K 31/05 |
| 2007/0101055 A1 | 5/2007 | Thorsen | |
| 2008/0213433 A1 | 9/2008 | Feller et al. | |
| 2009/0175984 A1 | 7/2009 | Rubin et al. | |
| 2009/0196951 A1 | 8/2009 | Brandborg | |
| 2010/0260912 A1 | 10/2010 | Norrie | |
| 2011/0104328 A1 | 5/2011 | Rubin et al. | |

FOREIGN PATENT DOCUMENTS

| | | |
|---|---|---|
| AU | 2007101055 A | 12/2007 |
| CN | 1699539 A | 11/2005 |

* cited by examiner

*Primary Examiner* — Kristin Vajda
(74) *Attorney, Agent, or Firm* — Maxwell L. Minch; GrayRobinson, P.A.

(57) ABSTRACT

Methods and formulations for infusing bioavailable flavonoid tinctures into food, beverage, cosmetic or drug products with minimal or no effect on the alcohol by volume of the product is provided. A flavonoid tincture includes an amount of trans-resveratrol, pterostilbene, quercetin, or combinations thereof, mixed with a solvent of pure, or majority by weight, ethanol or Dimethyl sulfoxide The tincture is added to various food and beverages to make a bioavailable amount of flavonoids to be absorbed and metabolized by the body providing demonstrated health benefits.

20 Claims, 3 Drawing Sheets

TINCTURE FOR INFUSING FLAVONOIDS AND METHODS OF USE

CROSS-REFERENCE TO RELATED APPLICATIONS

This application is a Continuation-In-Part of U.S. patent application Ser. No. 14/815,085, having a filing date of Jul. 31, 2015, which claims the benefit of U.S. Provisional Application No. 62/032,536, having filing date of Aug. 2, 2014, the disclosures of which are hereby incorporated by reference in their entirety and all commonly owned.

TECHNICAL FIELD

The present invention relates to tinctures for infusion into food, beverage, cosmetic or drug products and more specifically to a new and useful tincture for infusion containing homeopathic and anti-oxidative agents. The present invention further relates to methods for adding sufficient amount of tincture to provide sufficient and bioavailable amounts of homeopathic and anti-oxidative agents to a food, beverage, cosmetic or drug product, with minimal effect on the food, beverage, cosmetic or drug product's alcohol by volume (ABV).

BACKGROUND

Wine has played a positive role in maintaining human health by providing a sanitary source of water, through its psychoactive effects on the state of one's mind and by providing a reliable source of calories. In the early 1970's, the scientific and medical communities began taking an interest in the human health benefits of antioxidants including polyphenols. In 2003, trans-resveratrol was brought to the public's attention once it was reported that trans-resveratrol had life-extending properties. Concurrently it was advertised that trans-resveratrol is abundantly available in red wines as a result of the anti-oxidant being present in the skins of red grapes. With the intense interest in the health benefits of resveratrol by the scientific and medical communities has come a concurrent interest in the free market promotion of these proposed benefits. A 2008 study of the red wine market in Spain demonstrated that consumers were willing to pay a higher price for a resveratrol enhanced red wine than for its non-enhanced counterpart. Since then, many attempts have been made to enhance or add resveratrol to food and beverages to provide its health benefits.

While the interest in the health benefits of resveratrol has spiked so has the interest in the health benefits of pterostilbene and quercetin. While there are many flavonoids available, over 6,000, pterostilbene, implicated in a ticarcinogenesis, modulation of neurological disease, anti-inflammation, attenuation of vascular disease and amelioration of diabetes and quercetin used for treating conditions of the heart and blood vessels including hardening of the arteries, high cholesterol, heart disease and circulation problems have received special attention. Quercetin has become very popular because of the wide range of health benefits it offers in other areas including diabetes, cataracts, hay fever, peptic ulcer, schizophrenia, inflammation, asthma, gout, viral infections, chronic fatigue syndrome, preventing cancer and for treating chronic infections of the prostate.

Pterostilbene is found in almonds, vaccinium berries, and grape leaves and vines, but not in the actual grapes themselves and thus does not make their way into red wine. Quercetin is found in a variety of plants including red onion, radish, sweet potato, capers, fennel and more. Despite the high levels of flavonoids in many of these foods, studies have shown that the oral bioavailability is quite low and is rapidly cleared from the body. Because of the known anti-oxidant and anti-inflammatory health benefits as well as the support of the cardiovascular and nervous systems that comes from these flavonoids, a way to infuse them into food, beverage, cosmetic or drug products has become desired.

Flavonoids such as Resveratrol, Pterostilbene and quercetin have been found to have significant anti-oxidative effects on human metabolism and thus are believed to be efficacious in improving brain, heart, metabolic and other organ health. It has recently been confirmed that flavonoids such as resveratrol, pterostilbene, and quercetin in various combinations can act synergistically and additively. Thus, improving the benefits to human health over administering just a single flavonoid at a time.

There have been many forms of resveratrol, quercetin and pterostilbene enhanced products introduced to the market, but none provide for the flavonoids to be bioavailable for appropriate absorption by the human body, thus the "enhanced" qualities of the food or beverage becomes digested without being absorbed by the human body. Instead of being absorbed, the flavonoid additive is digested and eventually expelled from the body without significant absorption, thus making the enhancement of the food or beverage non-effective. Typically, flavonoid enhanced products simply include an amount of resveratrol or other flavonoid powder being added to the normal ingredients of the food or beverage since the resveratrol or other flavonoid powder adds very little to no flavor.

Currently, the common form of bioavailable resveratrol available to the consumer is provided from drinking red wine. It should be appreciated that merely ingesting an amount of resveratrol, whether in raw powder form, pill form, or as a suspended solid immixed within a liquid provides little, if any, bioavailability, thus the ingested resveratrol is digested and excreted without being available to the cells of the body. In fact, recent studies (Walle et al, Drug Metabolism and Disposition Vol 32, No. 12, pgs. 1377-1382 Jun. 7, 2004) have provided that "[a]ll attempts to find measurable levels of Resveratrol in plasma after the oral dose at any time point in [patients] failed." In oral dose scenarios, the free resveratrol essentially never makes it into the bloodstream.

A number of attempts have been made to provide for resveratrol or flavonoid enhanced beverages, however, many teach simply adding an amount of flavonoid or resveratrol powder to a beverage. These attempts fail to provide a flavonoid or resveratrol enhanced beverage because the flavonoid or resveratrol added little or no free flavonoid or resveratrol, rather it only becomes a suspended solid forming an aqueous solution, and becomes digested and excreted from the body with minimal absorption by the body. Moreover, while there have been many failed attempts to add flavonoid or resveratrol, nothing exists which provides a combination of a flavonoid and resveratrol enhanced beverage.

Thus, there remains an unmet need at providing an effective flavonoid enhanced, resveratrol enhanced, or a combination thereof, food, beverage, cosmetic or drug product that provides for a bioavailable amount of flavonoid or resveratrol to provide the homeopathic, anti-oxidative, anti-inflammatory and other benefits of flavonoids and resveratrol. There further remains an unmet need at providing an effective flavonoid or resveratrol enhanced food, beverage, cosmetic or drug product that provides a bioavailable amount of flavonoids or resveratrol while maintaining the alcohol by volume (ABV) of the enhanced food, beverage, cosmetic or drug product below any regulatory standards for required reporting.

SUMMARY OF INVENTION

A tincture of one or more flavonoids, a tincture of trans-resveratrol, or a combination thereof in a food grade or pharmaceutical grade ethanol base is provided. The ethanol base and flavonoid(s) and/or resveratrol tincture is added to any food, beverage, cosmetic or drug for infusing a bioavailable dose of resveratrol or flavonoid(s) to the food, beverage, cosmetic or drug. A method of making a tincture of resveratrol or flavonoid(s) and a solvent containing ethanol or other solvents including Dimethyl sulfoxide (DMSO) is also provided that includes mixing an amount of resveratrol or flavonoid(s) with an amount of the solvent containing ethanol or DMSO to form a mixture, agitating the resveratrol or flavonoid(s) and solvent mixture dissolving the flavonoid(s) or resveratrol into solution. The tincture is used to infuse a bioavailable dose of resveratrol or flavonoid(s) into a food, beverage, cosmetic or drug product.

DETAILED DESCRIPTION OF THE PREFERRED EMBODIMENTS

Figure 1:
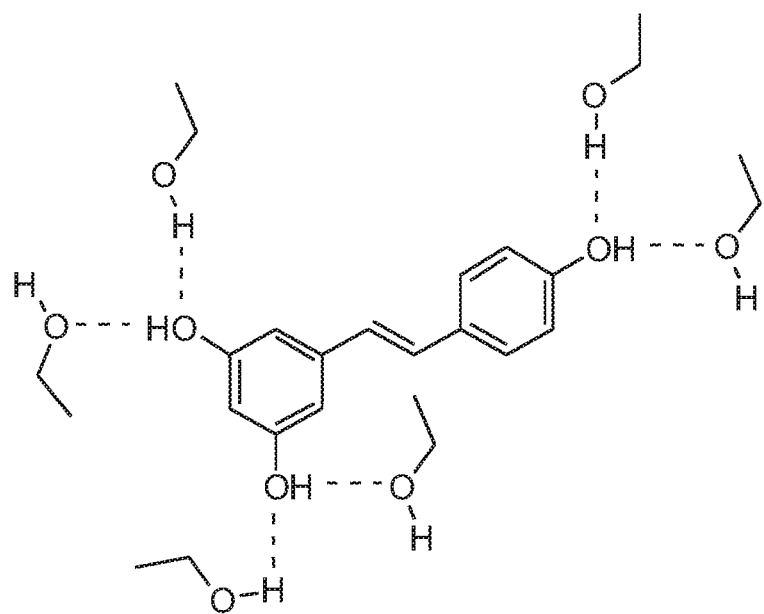
FIG. 1 is a representation of trans-resveratrol/Ethanol solution formed by mixing trans-resveratrol with pure ethanol.

The following detailed description is merely exemplary in nature and is in no way intended to limit the scope of the invention, its application, or uses, which may vary. The invention is described with relation to the non-limiting definitions and terminology included herein. These definitions and terminology are not designed to function as a limitation on the scope or practice of the invention, but are presented for illustrative and descriptive purposes only.

Various terms used throughout the specification and claims are defined as set forth below as it may be helpful to an understanding of the invention.

As used herein "mixture" shall mean a physical combination of two or more substances on which the identities are retained and are mixed but are not combined chemically.

As used herein, "food" or "beverage" may alternatively be a food, beverage, cosmetic or drug product.

As used herein, "ethanol" shall mean pure ethanol or a solvent containing a majority by weight of ethanol.

As used herein, "solvent" shall mean ethanol (as defined above), DMSO, or other solvent known in the art that is not harmful to humans in small quantities.

As used herein "tincture" shall mean an alcohol concentrate along with other materials that is used as an additive for a food or beverage.

As used herein, "flavonoid" shall mean those plant metabolites thought to provide health benefits through cell signaling pathways and antioxidant effects, including resveratrol, pterostilbene and quercetin.

As used herein "non-alcoholic beverage" shall mean a beverage having an alcoholic content by volume between 0.0% alcohol by volume (ABV) and 2.8% ABV. In some embodiments of the present invention, a "non-alcoholic beverage" is between 0.0% and 0.5% ABV.

As used herein "alcoholic beverage" shall mean any beverage with ABV content greater than that amount which is considered to be a non-alcoholic beverage.

As used herein "resveratrol" shall mean trans-resveratrol, cis-resveratrol, or dihydro-resveratrol. Trans-resveratrol having the structure provided in formula (I):

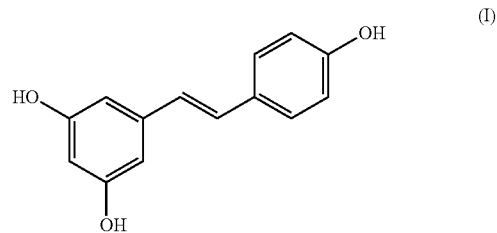 [SMILES: Oc1ccc(/C=C/c2cc(O)cc(O)c2)cc1]

(I)

As used herein "quercetin" shall mean quercetin having the structure provided in formula (II):

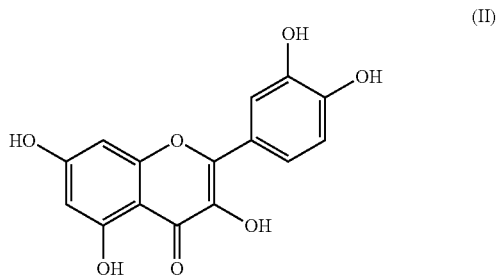 [SMILES: O=c1c(O)c(-c2ccc(O)c(O)c2)oc2cc(O)cc(O)c12]

(II)

As used herein "pterostilbene" shall mean trans-pterostilbene having the structure provided in formula (III):

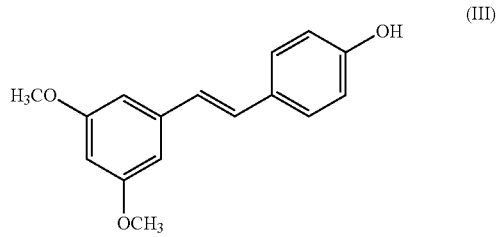 [SMILES: COc1cc(/C=C/c2ccc(O)cc2)cc(OC)c1]

(III)

As used herein "bioavailable" shall mean the amount of a particular dose of a drug product that is available within the blood stream for absorption or metabolization. In terms of resveratrol, bioavailable shall mean free trans-resveratrol and/or its conjugate forms or derivatives thereof available in a mixture or tincture.

As used herein "flavonoid(s)" shall mean resveratrol, quercetin, pterostilbene or combinations thereof.

The present invention provides a tincture which includes at least one flavonoid and solvent to be infused with a food, beverage, nutraceutical or cosmetic. It should be appreciated that by creating a flavonoid/solvent solution that a bioavailable dose of the flavonoid may be delivered to a subject orally. Without intending to be bound to a particular theory, it is believed that flavonoids, particularly resveratrol and pterostilbene, become hydrogen bonded upon making a solution with solvents, particularly ethanol or DMSO, in the present invention. The hydrogen bonded flavonoid can be added to any food or beverage and provide similar bioavailability as the tincture itself. It is further believed that the hydrogen bonded flavonoid is more easier metabolized by the body, thus causing the flavonoid to be absorbed into the bloodstream and increasing its bioavailability. In at least one embodiment a tincture is made of a solution of a flavonoid, or a combination of flavonoids, immixed with a solvent where the tincture is a homogeneous (single-phase) solution with the flavonoid solute hydrogen bonded to the solvent.

Several methods for making a tincture to provide a bioavailable amount of flavonoid are provided herein. A tincture of flavonoid and solvent is formed by mixing an amount of flavonoid with an amount of solvent to form a mixture and agitating the flavonoid and solvent mixture dissolving the flavonoid into solution. In at least one embodiment of the present invention, the solvent used is of food grade or pharmacy grade ethanol or DMSO. In at least one embodiment of the present invention, the ethanol or DMSO added to the tincture should be between 5% and 100% ethanol or DMSO. In at least one embodiment of the present invention, the ethanol is at least 160 proof. In at least one embodiment of the present invention, the ethanol is 200 proof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

It should be appreciated that while one may ingest an undiluted bioavailable tincture of flavonoid and ethanol directly, that such a high level of alcohol delivered directly to the body may have harmful effects which counteract the benefits from delivering bioavailable flavonoid. It is understood in the art that pure alcohol involves benzene azeotrope and is generally not for consumption.

In at least one embodiment of the present invention, the tincture may be added to a food or beverage. In at least one embodiment of the present invention, the tincture is added after all processing, distilling or heating has been performed on a food or beverage. In at least one embodiment of the present invention, the tincture is added to a food or beverage at the point of service of the food or beverage. In at least one embodiment, the tincture in encapsulated in a gel cap or immixed with a pharmaceutically acceptable carrier or gel and delivered as a pill or in a gel cap.

In some embodiments of the present invention, the tincture may be diluted with water. For example a resveratrol concentration in a solvent of a) 100% ethanol may be between 0 and 42 grams per liter of ethanol; b) 90% ethanol and 10% water may be between 0 and 32 grams per liter of ethanol; c) 80% ethanol and 20% water may be between 0 and 22 grams per liter of ethanol; d) 70% ethanol and 30% water is between 0 and 13 grams per liter of ethanol; e) 60% ethanol and 40% water is between 0 and 6.5 grams per liter of ethanol; 50% ethanol and 50% water is between 0 and 2.5 grams per liter of ethanol; f) 40% ethanol and 60% water is between 0 and 800 milligrams per liter of ethanol; g) 30% ethanol and 70% water is between 0 and 250 milligrams per liter of ethanol; h) 20% ethanol and 80% water is between 0 and 70 milligrams per liter of ethanol; i) 10% ethanol and 90% water is between 0 and 35 milligrams per liter of ethanol; and j) 5% ethanol and 95% water is between 0 and 18 milligrams per liter of ethanol.

Other additives may be introduced to the tincture to provide flavoring or other health benefits. In at least one embodiment of the present invention, the tincture may include one or more additional additives. In at least one embodiment of the present invention, additional additives may be water, spices, vitamins and minerals, color additives, flavor additives, or combinations thereof. In at least one embodiment spices may include pumpkin spice, cinnamon, sugar, sage, vanilla bean extract, or combinations thereof. In at least one embodiment, vitamins and minerals may include Thiamine hydrochloride, riboflavin (Vitamin B2), niacin, niacin amide, folate or folic acid, beta carotene, potassium iodide, iron or ferrous sulfate, alpha tocopherols, ascorbic acid, Vitamin D, amino acids (L-tryptophan, L-lysine, L-leucine, L-methionine), or combinations thereof. In at least one embodiment, color additives may include Orange B, Citrus Red No. 2, annatto extract, beta-carotene, grape skin extract, cochineal extract or carmine, paprika oleoresin, caramel color, fruit and vegetable juices or saffron. In at least one embodiment, flavor additives may be vinegar, citric acid, tartaric acid, malic acid, fumaric acid, lactic acid, high fructose corn syrup, hydrolyzed proteins, artificial sweeteners, or food extracts.

In some embodiments of the present invention the amount of flavonoid delivered in a tincture is to be of sufficient doses that are known to provide the health benefits associated with the selected flavonoid. In at least one embodiment, the flavonoid concentration is between 0.001 and 42 grams per liter of solvent. In at least one embodiment of the present invention, the flavonoid concentration is between 1 and 18 milligrams per liter of solvent. In at least one embodiment of the present invention, 1 to 100 milliliters of a 0.001 to 42 gram flavonoid per liter of solvent tincture is added to a 12 ounce beverage. In at least one embodiment 1 to 10 milliliters of the flavonoid tincture is added to a 12 ounce beverage.

Not being bound to any particular theory, a 25 mg dose of bioavailable trans-resveratrol is equivalent to 10-25 servings of red wine, understanding that red wines have variable amounts of bioavailable trans-resveratrol. Example 9, for instance, the red wine used for testing bioavailable trans-resveratrol was below the detection limits of the measuring device, while adding the inventive tincture provided 450 times more bioavailable resveratrol than what appeared in the red wine without the tincture.

It should be appreciated that adding an amount of tincture to a food or beverage may affect the alcohol content for which a food or beverage has been approved, or is desired. Thus, the present invention provides for a method of infusing a tincture of ethanol and flavonoid in a food or beverage, with minimal effect on the alcohol content of the food or beverage. Alternative solvents, such as DMSO may not have the same effects on alcohol content. In at least one embodiment of the present invention, a tincture of solvent and flavonoid is prepared and added to a beverage, and allowed sufficient time for the tincture to infuse with the beverage. In at least one embodiment of the present invention, the amount of tincture added to the beverage changes the amount of alcohol by volume (ABV) of the beverage between 0.01% and 1.0%. In at least one embodiment of the present invention, the amount of tincture changes the ABV of the beverage between 0.02% and 0.5%.

In certain embodiments of the present invention, the beverage is a non-alcoholic beverage. In at least one embodiment of the present invention, an amount of 10 milligram per liter tincture is added to a 12 ounce non-alcoholic beverage thus providing a bioavailable amount of flavonoid while minimally changing the alcohol by volume of the non-alcoholic beverage from 0.0% to 0.02%. In at least one embodiment of the present invention, a 0.1 milliliter dose of tincture is added to a 12 ounce non-alcoholic beverage thus providing a bioavailable amount of flavonoid while minimally changing the alcohol by volume of the non-alcoholic beverage from 0.0% to 0.02%. In at least one embodiment of the present invention, an amount of 100 milligram per liter tincture is added to a 12 ounce non-alcoholic beverage thus providing a bioavailable amount of flavonoid while minimally changing the alcohol by volume of the non-alcoholic beverage from 0.0% to 0.2%. In at least one embodiment of the present invention, a 1 milliliter dose of tincture is added to a 12 ounce non-alcoholic beverage thus providing a bioavailable amount of flavonoid while minimally changing the alcohol by volume of the non-alcoholic beverage from 0.0% to 0.2%.

In other embodiments of the present invention, the beverage is an alcoholic beverage. In at least one embodiment an amount of a 10 milligram per liter tincture is added to a 12 ounce alcoholic beverage thus providing a bioavailable amount of flavonoid while minimally changing the alcohol by volume of the alcoholic beverage from 5.0% to 5.02%. In at least one embodiment a 0.1 milliliter dose of tincture is added to a 12 ounce alcoholic beverage thus providing a bioavailable amount of flavonoid while minimally changing the alcohol by volume of the alcoholic beverage from 5.0% to 5.02%. In at least one embodiment an amount of a 100 milligram per liter tincture is added to a 12 ounce alcoholic beverage thus providing a bioavailable amount of flavonoid while minimally changing the alcohol by volume of the alcoholic beverage from 5.0% to 5.2%. In at least one embodiment a 1.0 milliliter dose of tincture is added to a 12 ounce alcoholic beverage thus providing a bioavailable amount of flavonoid while minimally changing the alcohol by volume of the alcoholic beverage from 5.0% to 5.2%.

In at least one embodiment, the tincture for a beverage infusion with 42 grams of flavonoid and a solvent containing 0% water and 100% solvent with a saturation of 42 g/L. In at least one embodiment a solution containing 42 grams of flavonoid in liter of solvent is passable through a 10 micron filter. In at least one embodiment the amount of bioavailable flavonoid present in a beverage containing the flavonoid tincture is 25 milligrams. In at least one embodiment 0.6 milliliters of tincture is added to a 355 milliliter (12 ounce) beverage to deliver a flavonoid dose of 25 milligrams. In at least one embodiment, the tincture for a food infusion is a solvent of 70% water and 30% ethanol, yielding 250 mg of flavonoid per liter of tincture.

EXAMPLES

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Example 1

A tincture of resveratrol and ethanol is made by immixing resveratrol and ethanol to provide 100 milligrams of resveratrol per liter of ethanol. A beer containing 5.0% ABV is poured into a glass. A direct measure of 0.1 mL dose of tincture is added to the 12 ounce beer. The added tincture raises the ABV of the beer to 5.02% while providing a bioavailable dose of resveratrol.

Example 2

Example 1 is repeated, but instead using a high-end mega-dose of 1.0 mL of tincture raising the ABV of the beer with tincture to 5.2%.

Example 3

A tincture of resveratrol and ethanol is made by immixing resveratrol and ethanol to provide 100 milligrams of resveratrol per liter of ethanol. A 12 ounce glass of water is poured and a syringe is used to measure a 0.1 mL dose of tincture and is added to the 12 ounces of water. The addition of the tincture raises the ABV of the water to 0.02% while providing a bioavailable dose of resveratrol.

Example 4

Example 3 is repeated, but instead using a high-end mega-dose of 1.0 mL of tincture raising the ABV of the water with tincture to 0.2%.

Example 5

Figure 2:
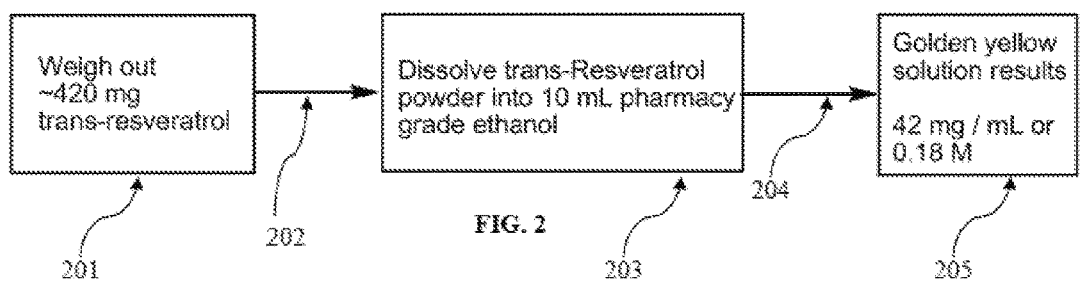
FIG. 2 is a block diagram providing an example of at least one embodiment of the present invention illustrating the method of 201 weighing approximately 420 milligrams trans-resveratrol, 202 measuring an amount of solvent containing 10 milliliters of pharmacy grade ethanol, 203 dissolving the 201 trans-resveratrol powder in the 202 solvent and 205 providing a golden yellow tincture containing resveratrol dissolved in ethanol. In at least one embodiment the solution is 204 passed through a 10 micron filter to remove any undissolved resveratrol and any other impurities or suspended solids contained in the solution. In at least one embodiment the solution is 204 agitated to aide in the dissolving of the 201 trans-resveratrol powder in the 202 solvent containing at least 10 milliliters of ethanol.
Figure 3:
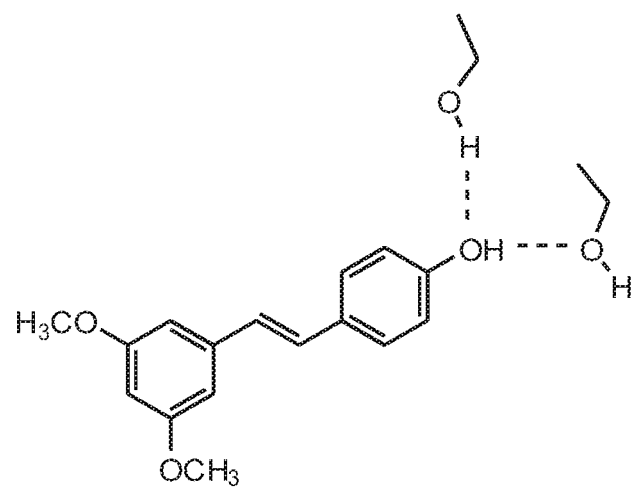
FIG. 3 is a representation of pterostilbene/Ethanol solution formed by mixing pterostilbene with pure ethanol.

FIG. 2 provides a method for making a tincture. First 201 approximately 420 milligrams of trans-resveratrol powder is weighed. Next 202 an amount of solvent containing 10 milliliters of pharmacy grade ethanol is measured, immixed and agitated with the 201 approximately 420 milligrams of trans-resveratrol powder. The solution is agitated causing an amount of 203 the trans-resveratrol powder to dissolve in the solvent. The mixed solution appears 205 golden yellow in color that contains 42 milligrams trans-resveratrol per milliliter of ethanol contained in the solvent.

Example 6

Example 5 is repeated, but includes the additional step 204 of passing the solution through a 10 micron filter to remove any undissolved resveratrol and any other impurities contained in the resveratrol powder.

Example 7

A tincture is made containing concentrated (near-saturated at 25° C.) resveratrol and ethanol tinctures of 420 mg/10 mL (42.0 mg/mL). To deliver a 25 mg dose, 0.60 mL of tincture is required regardless of volume of beverage.

Example 8

A tincture of trans-resveratrol with ethanol is prepared with food grade or pharmaceutical grade 180 to 200 proof ethanol. Observations under multiple environmental settings confirmed the stability of the tincture created. Using medical grade measuring devices, the tincture was added to various beverages in volumes necessary to replicate and exceed the amount of trans-resveratrol in a typical serving of red wine from the Mediterranean stock. Observations demonstrated that there was no precipitation, no change in color, no change in taste and calculations confirmed that the amount of increase in alcohol by volume was maintained below any regulatory standards for required reporting.

Example 9

A tincture of trans-resveratrol with ethanol is prepared with food grade 200 proof ethanol. The trans-resveratrol tincture is was prepared by adding 421.5 mg trans-resveratrol to 10 mL of 200 proof (100%) food grade ethanol. This resulted in a clear, golden-colored solution with concentration of 42.15 mg/mL.

A dose of 25 mg of trans-resveratrol is delivered to a serving volume of various drinks including red wine, white wine, beer (Yuengling), spirits such as vodka and bourbon (Jim Beam), energy drinks (5 Hour Energy), sodas (diet Coke, Coke, Sprite) and orange juice (Tropicana). To deliver 25 mg of trans-resveratrol, 0.60 milliliters of trans-resveratrol tincture is required (42.15 mg/mL×0.60 mL=25.29 mg). An amount of the trans-resveratrol tincture is added to each beverage and is calculated based on the volume of the serving. The serving volume for a glass of wine is 187 mL. The serving volume for a glass of wine plus the 0.60 mL of trans-resveratrol tincture was divided by the dose of trans resveratrol 25.29 mg/187.6 mL=0.1348 mg/mL. 0.1348 mg/mL was then multiplied by 1000 ug/mg to get the amount in ug/mL, 0.1348 mg/mL×1000 ug/mg=134.8 ug/mL. Similar calculations are performed for the remaining beverages. For beer, sodas and orange juice, the serving volume is 355 mL for each beverage, resulting in 71.1 ug/mL of trans-resveratrol to be infused into each beverage. For spirits, the serving volume for spirits is 50 mL, resulting in 499.8 ug/mL of trans-resveratrol infused. For Five Hour Energy®, the serving volume is 57 mL, resulting in 439.1 ug/mL of trans-resveratrol infused. A red wine blank was used as a control in order to show natural resveratrol being present in the beverage.

After the calculations are completed a syringe is used to transfer 0.6 mL of trans-resveratrol tincture to a serving volume of each beverage. The tincture is delivered to each serving volume below the surface of the liquid. In all cases the trans-resveratrol tincture appears to dissolve as a homogenous solution. All beverages receiving the tincture are thoroughly mixed, and a few milliliters of each are transferred to amber-colored sample vials. Samples are stored from each beverage in a refrigerator for analysis.

During analysis the percent of the free trans-resveratrol recovered in the various drinks was determined via HPLC/HESI-MS/MS and HPLC/UV (305 nm).

The results of this experiment are presented in Table 1.

TABLE 1

| Drink# | Sample: | [t-Rsv] (ug/mL) | | | % Theory | |
|---|---|---|---|---|---|---|
| | | Theor | MS/MS | UV | MS/MS | UV |
| 1 | red wine blank | 0 | <<<spike | | n/a | n/a |
| 2 | Red Wine, spiked | 134.8 | 45.8 | 100.0 | 33.9 | 74.2 |
| 3 | White wine spiked | 134.8 | 63.8 | 108.5 | 47.4 | 80.5 |

TABLE 1-continued

| Drink# | Sample: | [t-Rsv] (ug/mL) | | | % Theory | |
|---|---|---|---|---|---|---|
| | | Theor | MS/MS | UV | MS/MS | UV |
| 4 | Beer; Yuengling Summer Wheat | 71.1 | 34.0 | 74.3 | 47.8 | 104.5 |
| 5 | Vodka (V), AB Brand | 499.8 | 489.3 | 549.0 | 97.9 | 109.9 |
| 6 | Bourbon (BO), Jim Beam | 499.8 | 584.0 | 534.6 | 116.9 | 107.0 |
| 7 | 5H, Grape | 439.1 | 470.4 | 473.8 | 107.1 | 107.9 |
| 8 | Diet Coke | 71.1 | 57.1 | 68.7 | 80.2 | 96.6 |
| 9 | Coke | 71.1 | 49.1 | 64.7 | 69.0 | 90.9 |
| 10 | Sprite | 71.1 | 53.8 | 61.4 | 75.7 | 86.3 |
| 11 | OJ, Tropicana | 71.1 | 21.1 | 41.4 | 29.7 | 58.2 |

It is observed that all beverages receiving the tincture show measurable concentrations of trans-resveratrol. The red wine blank, which is not spiked, is analyzed for natural trans-resveratrol background. While trans-resveratrol is detected in the red wine blank, it is at the instrument's minimum detection limit. Integration of peak areas show the ratio of spiked red wine to unspiked red wine was ~450. Moreover, the trans-resveratrol in solution is bioavailable because the detection methods can only detect free and unbound trans-resveratrol.

Generally, UV detection reveals higher trans-resveratrol concentrations than did MS/MS detection. MS/MS detection focuses on the 228 mass number, resveratrol's molecular weight. UV detection at a fixed wavelength (305 nm) shows detection of the molecule's conjugated core which includes the two aromatic rings and the adjoining C=C pi bond. Notwithstanding, the recovery values were generally moderate 30-70% to high 70-100%.

Example 10

A tincture of trans-resveratrol with ethanol is prepared with food grade 200 proof ethanol. To deliver 25 mg of trans-resveratrol, 0.60 milliliters of trans-resveratrol tincture is required (42.15 m/mL×0.60 mL=25.29 mg). The serving volume for spirits is 50 mL. 25.29 mg/50.6 mL resulting in 499.8 ug/mL of trans-resveratrol to infuse the spirits with. A syringe is used to transfer 0.6 mL of trans-resveratrol tincture into the vodka and bourbon. The infused drinks show measurable concentrations of trans-resveratrol. The percent recovery of free trans-resveratrol recovered in the vodka during analysis is 97.9% MS/MS and 109.9% UV, and in the bourbon is 116.9% MS/MS and 107% UV. It is appreciated that the percent recovery in some instances is greater than 100% because of +/−17% error because of the techniques used to measure trans resveratrol. As a result these values can be considered to be 100% recovery in the vodka and bourbon beverages. These results show the bioavailability of the trans-resveratrol tincture added to beverages.

Example 11

25 mg of trans-resveratrol powder is added to a serving volume of various drinks including red wine, white wine, beer (Yuengling), spirits such as vodka and bourbon (Jim Beam), energy drinks (5 Hour Energy), sodas (diet Coke, Coke, Sprite) and orange juice (Tropicana). In all cases the trans-resveratrol appears to suspend in solution forming a cloudy layer. All beverages receiving the powder are thoroughly mixed. Each beverage is passed through a 10 micron filter to remove any undissolved resveratrol and any other impurities contained in the resveratrol powder. A few milliliters of each beverage are transferred to amber-colored sample vials. Samples are stored from each beverage in a refrigerator for analysis.

During analysis the percent of the free trans-resveratrol recovered in the various drinks was determined via HPLC/(+)ESI-MS/MS and HPLC/UV (305 nm). It is observed that none of the non-alcoholic beverages (energy drink, sodas, and orange juice) receiving the powder show any measurable concentrations of trans-resveratrol. This differs from the results provided in Example 9 drastically, showing that merely adding powder resveratrol to a beverage does not provide a bioavailable amount of resveratrol. Notwithstanding, it was observed that the alcoholic beverages(red wine, white wine, beer and spirits) receiving the powdered resveratrol did have some amount of bioavailable resveratrol, but below the minimum detection limits of the devices, and thus could not be quantified. This again shows a drastic difference from the results of Example 9, confirming that merely adding resveratrol powder to a beverage minimally delivers a bioavailable amount of resveratrol as compared to the inventive tincture.

Example 12

Examples 1 through 9 are repeated using the solvent DMSO and the flavonoid pterostilbene.

Example 13

A tincture of pterostilbene and solvent is made by dissolving approximately 420 mg trans-pterostilbene powder into 10 mL of pharmacy grade ethanol.

Example 14

A tincture of resveratrol, pterostilbene, and ethanol is made by combining separate volumes of tincture of resveratrol and tincture of pterostilbene in a range of the following volume resveratrol to volume pterostilbene ratios: 9:1, 4:1, 7:3, 3:2, 1:1, 2:3, 3:7, 1:4, and 1:9.

A similar study of that of Example 9 was conducted using above combinations of resveratrol and pterostilbene. The results of this experiment are presented in Table 2.

TABLE 2

Binary Tincture Range of Formulation: R + Pt (vol R:vol Pt)

| % R | % Pt | Ratio R:Pt | Conc (mg/mL) R | Conc (mg/mL) Pt |
|-----|------|-----------|----------------|-----------------|
| 100 | 0    | Pure R    | 42.0           | 0.0             |
| 90  | 10   | 9:1       | 37.8           | 4.2             |
| 80  | 20   | 4:1       | 33.6           | 8.4             |
| 70  | 30   | 7:3       | 29.4           | 12.6            |
| 60  | 40   | 3:2       | 25.2           | 16.8            |
| 50  | 50   | 1:1       | 21.0           | 21.0            |
| 40  | 60   | 2:3       | 16.8           | 25.2            |
| 30  | 70   | 3:7       | 12.6           | 29.4            |
| 20  | 80   | 1:4       | 8.4            | 33.6            |
| 10  | 90   | 1:9       | 4.2            | 37.8            |
| 0   | 100  | Pure Pt   | 0.0            | 42.0            |

Example 14

A 1.0 mL volume of the resulting tincture in Example 13 contains the following range of mg doses of resveratrol and pterostilbene respectively: 37.8, 4.2; 33.6, 8.4; 29.4, 12.6; 25.2, 16.8; 21.0, 21.0; 16.8, 25.2; 12.6, 29.4; 8.4, 33.6; and 4.2, 37.8.

Example 15

A tincture of resveratrol, quercetin, and ethanol is made by dissolving 1.5 mg of quercetin powder into 1.0 mL of tincture of resveratrol. The resulting tincture contains 42 mg resveratrol and 1.5 mg quercetin.

Example 16

A tincture of resveratrol, pterostilbene, and quercetin is made by dissolving 1.5 mg of quercetin powder into 1.0 mL of the tincture of resveratrol, pterostilbene, and ethanol of any ratio over the range cited in Example 13.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A method of making a tincture for infusing a beverage, food, cosmetic or drug to provide a bioavailable dose of one or more flavonoids, the method comprising:
    mixing an amount of one or more flavonoids with an amount of solvent to form a mixture;
    agitating the one or more flavonoids and solvent mixture; and
    adding an additional amount of solvent and repeat agitation of the mixture until said one or more flavonoids is dissolved in the solvent.

2. The method of claim 1 further comprising filtering the solvent and flavonoid solution to remove any undissolved flavonoid, any impurities, any other suspended solids, or combinations thereof.

3. The method of claim 1 wherein the solvent is ethanol or Dimethyl sulfoxide (DMSO).

4. The method of claim 1 wherein the flavonoid concentration is between 0.001 and 42 grams per liter of solvent.

5. A method of infusing a tincture, the method comprising:
    preparing a tincture of solvent being a majority by weight solvent and flavonoid;
    adding an amount of the tincture to a food, beverage, cosmetic or drug product; and
    allowing sufficient time for the tincture to infuse with the food, beverage, cosmetic or drug product.

6. The method of claim 5 wherein the solvent is ethanol and the amount of tincture changes the amount of alcohol by volume (ABV) of the food, beverage, cosmetic or drug product between 0.01% and 1.0%.

7. The method of claim 6 wherein the solvent is ethanol and the amount of tincture changes the ABV of the food, beverage, cosmetic or drug product between 0.02% and 0.5%.

8. A tincture for infusing a beverage to provide a bioavailable dose of flavonoid, the tincture comprising:
a majority by weight solvent; and
an amount of flavonoid in solution.

9. The tincture of claim 8, wherein said flavonoid is resveratrol, pterostilbene, quercetin or combinations thereof.

10. The tincture of claim 8 wherein the solvent is a majority by weight Dimethyl sulfoxide (DMSO) or ethanol.

11. The tincture of claim 8, further comprising additional additives, wherein said additional additives are water, spices, vitamins and minerals, color additives, flavor additives, or combinations thereof.

12. The tincture of claim 8 wherein said spices are pumpkin spice, cinnamon, sugar, sage, vanilla bean extract, or combinations thereof.

13. The tincture of claim 8 wherein said vitamins and minerals are Thiamine hydrochloride, riboflavin (Vitamin B2), niacin, niacinamide, folate or folic acid, beta carotene, potassium iodide, iron or ferrous sulfate, alpha tocopherols, ascorbic acid, Vitamin D, amino acids (L-tryptophan, L-lysine, L-leucine, L-methionine), or combinations thereof.

14. The tincture of claim 8 wherein said color additives are Orange B, Citrus Red No. 2, annatto extract, beta-carotene, grape skin extract, cochineal extract or carmine, paprika oleoresin, caramel color, fruit and vegetable juices, saffron or combinations thereof.

15. The tincture of claim 8 wherein said flavor additives are vinegar, citric acid, tartaric acid, malic acid, fumaric acid, lactic acid, high fructose corn syrup, hydrolyzed proteins, artificial sweeteners, or food extracts.

16. The tincture of claim 8 wherein the flavonoid concentration in a solvent of 50%-100% ethanol is between 0.001 and 42 grams per liter of ethanol.

17. The tincture of claim 10 wherein the flavonoid concentration in a solvent containing 5%-40% ethanol is between 1 and 800 milligrams per liter of ethanol.

18. The tincture of claim 10 wherein said tincture is encapsulated in a gelatin shell.

19. The tincture of claim 18 wherein, said tincture is infused with a pharmaceutically acceptable carrier or gelatin filling.

20. The tincture of claim 10 wherein said tincture comprises 1.5 mg quercetin in powder form added to 1.0 mL tincture of resveratrol or pterostilbene, or a 1.0 mL tincture of resveratrol and pterostilbene.

* * * * *